United States Patent
Lin Charna

(10) Patent No.: US 10,376,422 B2
(45) Date of Patent: Aug. 13, 2019

(54) SYSTEM AND METHOD FOR DETECTING WETNESS OF ARTICLE USED BY A CARE-RECEIVER

(71) Applicant: Hello Nurse Medical Innovation, Inc., Irvine, CA (US)

(72) Inventor: Sharon Lin Charna, New Taipei (TW)

(73) Assignee: Hello Nurse Medical Innovations, Inc., Irvine, CA (US)

(*) Notice: Subject to any disclaimer, the term of this patent is extended or adjusted under 35 U.S.C. 154(b) by 18 days.

(21) Appl. No.: 15/795,299

(22) Filed: Oct. 27, 2017

(65) Prior Publication Data
US 2018/0049926 A1    Feb. 22, 2018

Related U.S. Application Data

(63) Continuation-in-part of application No. 15/233,985, filed on Aug. 11, 2016.

(30) Foreign Application Priority Data

Aug. 13, 2015    (TW) .............................. 104213035 U

(51) Int. Cl.
*A61F 13/42*    (2006.01)
*A61B 5/00*    (2006.01)
*A61B 5/11*    (2006.01)
*H04B 1/3888*    (2015.01)
(Continued)

(52) U.S. Cl.
CPC ............ *A61F 13/42* (2013.01); *A61B 5/0022* (2013.01); *A61B 5/1117* (2013.01); *H04B 1/3888* (2013.01); *H04W 4/80* (2018.02); *A61F 2013/424* (2013.01); *H04B 2001/3894* (2013.01)

(58) Field of Classification Search
CPC .... A61F 13/42; A61F 2013/424; H04W 4/80; A61B 5/0022; A61B 5/1117; H04B 1/3888; H04B 2001/3894
See application file for complete search history.

(56) References Cited

U.S. PATENT DOCUMENTS

2013/0169417 A1* 7/2013 Sugano .................... G06K 7/01
                                                        340/10.1
2016/0095758 A1* 4/2016 Haire ...................... A61F 13/42
                                                        600/301
(Continued)

*Primary Examiner* — Munear T Akki
(74) *Attorney, Agent, or Firm* — J.H. Lin Patent Law P.C.; John H. Lin

(57) ABSTRACT

A system for detecting wetness of article used by a care-receiver is provided, comprising: a radio frequency identity (RFID) tag to be attached onto an outer surface of an article used by the care-receiver, and a RFID reader. The RFID reader includes at least one first antenna module, a processor unit and a first wireless communication module. And the system further comprises a protective unit is configured for accommodating the RFID reader and buffering external pressure on the RFID reader to protect the RFID reader. The RFID reader is configured for being disposed on a back of a cushion. The first wireless communication module is configured to send a detection signal (excitation signal) through the first antenna module to the RFID tag and the processor unit determines the water content (%) of the article at the usage time (t) by using the RSSI(0) and RSSI(t).

20 Claims, 11 Drawing Sheets

(51) Int. Cl.
   *H04W 4/80*   (2018.01)
   *H04B 1/38*   (2015.01)

(56) References Cited

U.S. PATENT DOCUMENTS

2017/0098044 A1\* 4/2017 Lai .................... G06K 19/0716
2018/0116878 A1\* 5/2018 MacNaughton ........ A61F 13/42

\* cited by examiner

SYSTEM AND METHOD FOR DETECTING WETNESS OF ARTICLE USED BY A CARE-RECEIVER

CROSS-REFERENCES TO RELATED APPLICATIONS

The present application is a continuation-in-part application of U.S. patent application Ser. No. 15/233,985 filed on Aug. 11, 2016, which claims the benefit of Taiwanese Patent Application No. 104213035 filed on Aug. 13, 2015. The entire contents of all the above are hereby incorporated by reference.

BACKGROUND

Technical Field

The invention relates to technology of a system and method for caring a care-receiver and determining a state of the care-receiver, and in particular, treating a care-receiver and detecting a wetness state of an absorbent article for a care-receiver and/or a fall warning state for a care-receiver, wherein the absorbent article may be any diaper (such as adults diapers), urine pads.

Related Art

The technology of diapers equipped with detection devices for wetness detection arises from the needs for long-term care for babies, patients, or disabled elders so as to reduce the burden of work on the caregivers and to deliver better services to the care-receivers.

Conventional diapers with detection devices are complicated in structure. Some of them require sensors and antennas disposed on one side of the diaper in contact with users' skin, which may make the users feel uncomfortable. Others are modified by disposing sensors and antennas inside the diapers to avoid contact with users' skin. For example, US Patent Publication No. 2014/0276504 A1 discloses a sensor disposed in an incontinence pad to detect the presence of moisture. The disposition of the sensor inside the pad might adversely affect the sensing accuracy due to the interference of moisture source. Aside from, the sensor, even if implemented with an RFID tag, has to be discarded together with the polluted pad, and cannot be reused. In addition to requiring the users using such diapers, a determination device, which may have the similar size as a telephone, is required to be disposed on the bed or a fixed position on the room in order to inform the caregivers of whether the diaper is wet. Such systems of detection and determination occupy space and require high hardware cost.

SUMMARY

Accordingly, a system and method for detecting wetness of article used by a care-receiver are provided, which can be employed to care and determine a state of a care-receiver, such as a wetness state of an absorbent article. The article may be any type of articles, for example, diapers (such as adults' diaper, babies' diapers, and so on), urine pads, and so on.

According to an embodiment of the invention, provided a system for detecting wetness of article used by a care-receiver, comprising: a radio frequency identity (RFID) tag to be attached onto an outer surface of an article used by the care-receiver, wherein the article comprises at least an absorbent material; and a RFID reader which comprises a first antenna module; a first wireless communication module, coupled to the first antenna module, configured to send a detection signal (excitation signal) through the first antenna module to the RFID tag, and configured to receive a response signal from the RFID tag in response to the sent detection signal, through the first antenna module; and a processor unit configured to exhibit a signal strength indicator (RSSI) corresponding to a response signal from the RFID tag in response to the sent detection signal (excitation signal), through the first antenna module, and denoting as RSSI(t) of the article after being used for a usage time (t), and determining the water content (%) of the article at the usage time (t) by calculating from following formula (I) by using the RSSI(0) and RSSI(t):

$$\text{Water content (\%)} = \{RSSI(0) - RSSI(t)\}/0.32 \qquad (I)$$

wherein RSSI(0) is a received signal strength indicator (RSSI) of the response signal from the RFID tag in response to the excitation signal while the article prior to be used at initial time (t=0); and RSSI(t) is a received signal strength indicator (RSSI) of the response signal from the RFID tag in response to the excitation signal at a usage time(t) of the article being used.

In an embodiment, the system for detecting wetness of article used by a care-receiver further comprises an alarming unit configured to notify a care-giver while wetness is higher than a preset value.

In an embodiment, the system for detecting wetness of article used by a care-receiver further comprises: a second antenna module and a second wireless communication module; the second wireless communication module is electrically coupled to the first wireless communication module and the second antenna module; wherein the first wireless communication module utilizes the second antenna module and the second wireless communication module so as to communicate with a computing device in a wireless network, and sends the state of the care-receiver to the computing device.

According to another embodiment of the invention, the RFID reader is configured to be disposed on a back of a cushion and is utilized for being disposed on a back of a cushion.

In an embodiment, the article comprises: an absorbent material layer having variable permittivity based on the content of moisture in the absorbent material layer; a contact layer disposed at a side of the absorbent material layer for contact with skin of the care-receiver; and a protective layer disposed at an opposite side of the absorbent material layer to the contact layer, and the article may be a diaper or urine pad.

In an embodiment, the RFID tag is attached onto an outer surface of the protective layer opposite to the absorbent material layer.

According to another embodiment of the invention, a method for detecting wetness of article used by a care-receiver is provided; the method comprising the steps of: (a) attaching the RFID tag onto outer surface of an article to be detected, wherein the article includes an absorbent material, and the RFID tag is configured to exhibit different sensitivities to the electromagnetic wave signal in response to different permittivities of the article; (b) exciting a RFID tag with an excitation signal (ES); (c) wirelessly detecting a received signal strength indicator (RSSI) of the response signal from the RFID tag in response to the excitation signal while the article is dry or prior to be used at initial time (t=0) and denoting as initial value RSSI(0) of the article; (d)

wirelessly and timely detecting a received signal strength indicator (RSSI) of the response signal from the RFID tag of the article, in response to the excitation signal and denoting as RSSI(t) of the article after being used for a usage time (t); and (e) determining the water content (%) of the article at the usage time (t) by calculating from following formula (I) by using the RSSI(0) and RSSI(t):

$$\text{Water content (\%)} = \{RSSI(0) - RSSI(t)\}/0.32 \qquad (I)$$

wherein RSSI(0) is a received signal strength indicator (RSSI) of the response signal from the RFID tag in response to the excitation signal while the article prior to be used at initial time (t=0); and RSSI(t) is a received signal strength indicator (RSSI) of the response signal from the RFID tag in response to the excitation signal at a usage time(t) of the article being used.

In an embodiment, the absorbent material layer and the RFID tag are not contact with each other.

For better understanding of the above and other aspects of the invention, a plurality of embodiments or examples will be taken with accompanying drawings to provide detailed description as follows.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be implemented with or without these specific details. Furthermore, one skilled in the art can readily appreciate that it is contemplated that the embodiments can be modified or varied and still remain within the spirit and scope of the various embodiments disclosed herein.

The following will provide a plurality of embodiments so as to describe different aspects of implementations of the system for detecting wetness of article used by a care-receiver.

According to an embodiment of the invention, provided is a system for detecting wetness of article used by a care-receiver, comprising: a radio frequency identity (RFID) tag to be attached onto an outer surface of an article used by the care-receiver and a RFID reader. The RFID reader includes a first antenna module, a first wireless communication module, and a processor unit configured to exhibit a signal strength indicator (RSSI) corresponding to a response signal from the RFID tag in response to the sent detection signal (excitation signal), through the first antenna module, and denoting as RSSI(t) of the article after being used for a usage time (t); the first wireless communication module and the first antenna module are electrically coupled. And the RFID reader further comprises a protective unit, which covers at least the RFID reader, is for accommodating the RFID reader and for buffering external pressure on the RFID reader so as to protect the RFID reader. The RFID reader for a care-receiver is utilized for being disposed on a back of a cushion. The first wireless communication module sends a detection signal through at least the first antenna module so as to communicate with a radio frequency identity (RFID) tag disposed on a diaper. After the detection signal is sent, the RFID reader determines whether a response signal is received or information of the response signal is read so as to determine a state of the care-receiver.

The RFID reader of the system for detecting wetness of article used by a care-receiver may further include: a second antenna module and a second wireless communication module. The second wireless communication module is electrically coupled to the first wireless communication module and the second antenna module; wherein the first wireless communication module utilizes the second antenna module and the second wireless communication module so as to communicate with a computing device in a wireless network, and sends the state of the care-receiver to the computing device.

Figure 1A:
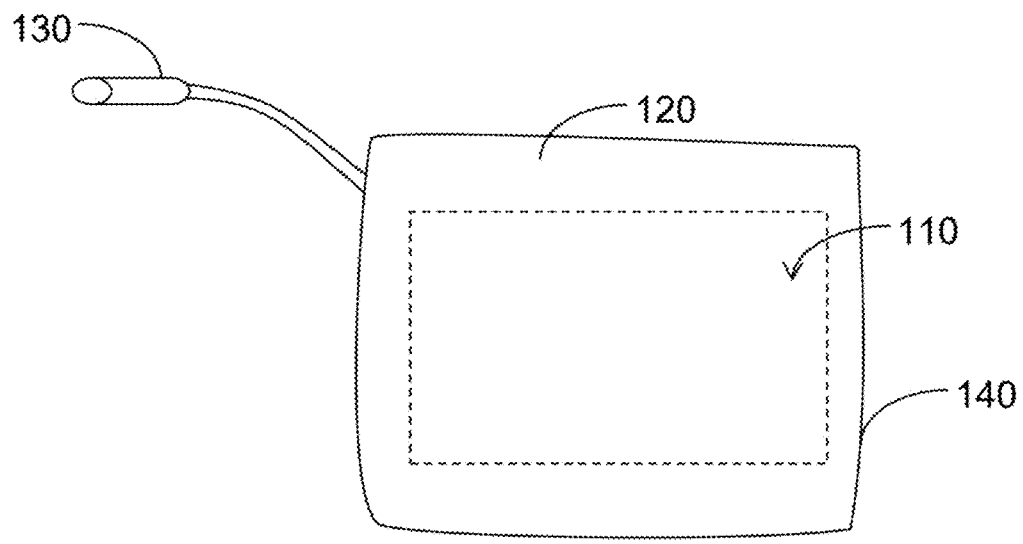
FIGS. 1A-1C illustrate schematic diagrams of a system for detecting wetness of article used by a care-receiver according to an embodiment of the invention.
Figure 1B:
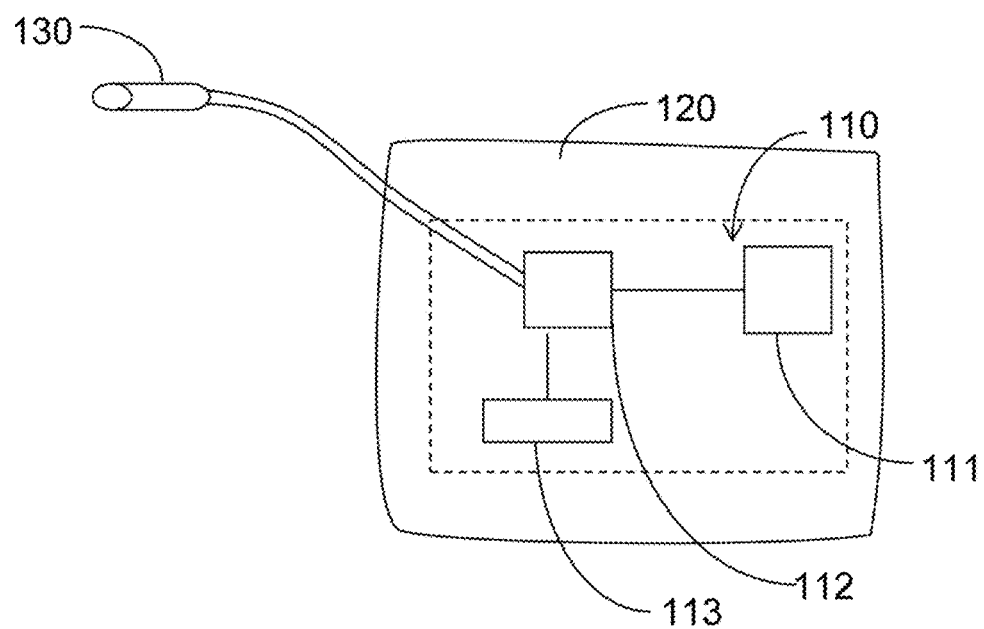
Figure 1C:
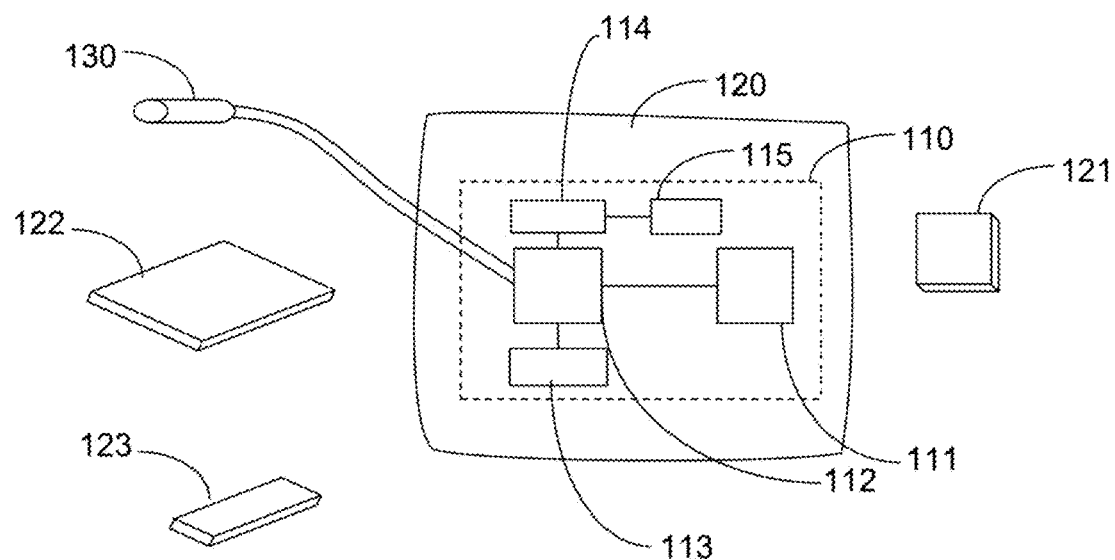

FIGS. 1A-1C illustrate schematic diagrams of a system for detecting wetness of article used by a care-receiver according to an embodiment of the invention. As shown in FIG. 1A, the system for detecting wetness of article used by a care-receiver includes a RFID tag (not shown), a RFID reader 110 (wherein a region inside is indicated in dashed lines), a protective unit 120, and an input part 130. RFID reader 110 comprises a processor unit 111, a first wireless communication module 112, and a first antenna module 113, and the RFID reader 110 is disposed inside the protective unit 120. In addition, for the sake of waterproof and safety, the system for detecting wetness of article used by a care-receiver further includes a protective cover 140 which wraps the RFID reader 110 and the protective unit 120. The input part 130, electrically coupled to the RFID reader 110, serves as an input interface, which, for example, includes at least one of a power input, a data interface, an input key.

FIG. 1B is a schematic diagram illustrating the system for detecting wetness of article used by a care-receiver when the protective cover 140 is removed. The protective unit 120 covers the RFID reader 110, and a liftable part, such as liftable parts 121, 122, and 123, is provided on a region in the protective unit 120 corresponding to at least one portion of the RFID reader 110. As shown in FIG. 1C, when any one of the liftable parts 121, 122, and 123 is lifted, the portion of the processor unit 111, the first wireless communication module 112, and the first antenna module 113 (such as the circuit or antenna) is exposed, and thus maintenance technicians or engineers can perform detection or maintenance tasks with respect to the portion of the RFID reader 110 (such as the circuit or antenna).

For example, in FIG. 1C, the RFID reader 110 includes a processor unit 111, a first antenna module 113, a first wireless communication module 112, a second antenna module 115, and a second wireless communication module 114. The first wireless communication module 112 and the first antenna module 113 are electrically coupled.

Figure 2A:
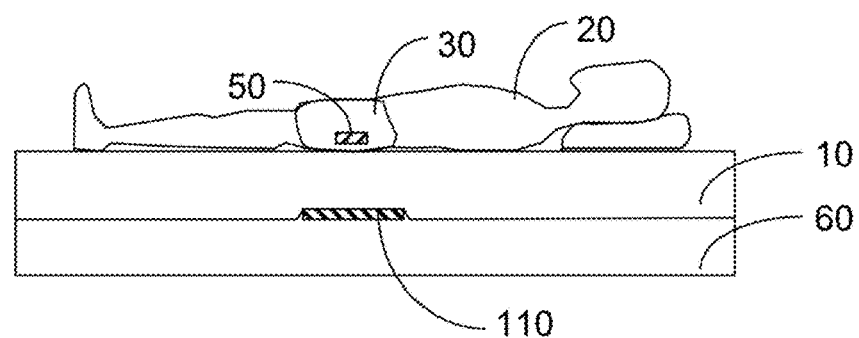
FIGS. 2A-2B illustrate schematic diagrams of an embodiment of the state determination system for detecting wetness of article used by a care-receiver, disposed on a mattress.
Figure 2B:
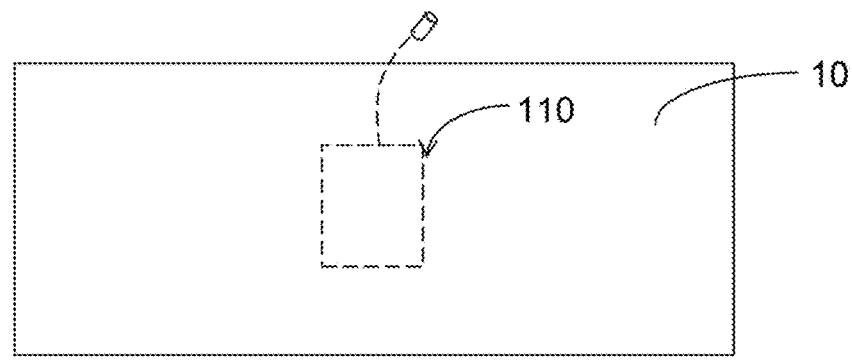
Figure 3A:
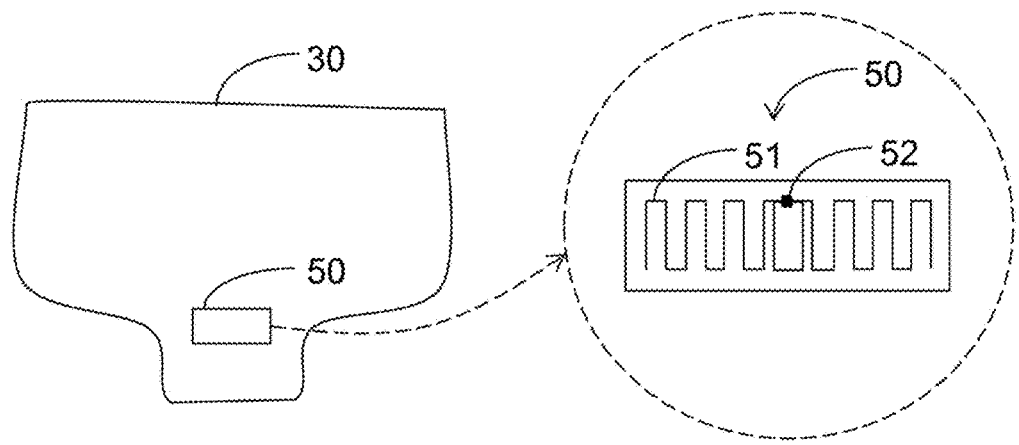
FIG. 3A illustrates an RFID tag disposed on a diaper.

The RFID tag and the RFID reader of the system for detecting wetness of article used by a care-receiver according to the invention can be employed to determine the state of a care-receiver, such as a wetness state of an article and/or a state of fall warning for the care-receiver, and so on. The article may be any type of articles, for example, diapers (such as adults' diaper, babies' diapers, and so on), urine pads, and so on. For the sake of illustration, the following embodiments will take a diaper as the article. As shown in FIG. 2A, the RFID reader 110 for a care-receiver is utilized for being disposed on the back of a cushion 10 (such as a mattress) so as to perform state determination on a diaper 30 on a user 20 (so called a care-receiver) lying on a front surface of the cushion 10 (such as a mattress). FIG. 2B is a top view illustrating a main body of the RFID 110 for a care-receiver disposed on the back of the mattress, wherein an input part 130 can be exposed outside the mattress. FIG. 3A is a schematic diagram illustrating an RFID tag 50 disposed on an outer surface of the diaper 30.

Referring to FIG. 2A, the method for detecting wetness of article used by a care-receiver is comprising the steps of (a) attaching the RFID tag onto outer surface of an article to be detected, wherein the article includes an absorbent material, and the RFID tag is configured to exhibit different sensitivities to the electromagnetic wave signal in response to different permittivities of the article; (b) exciting a RFID tag with an excitation signal (ES); (c) wirelessly detecting a received signal strength indicator (RSSI) of the response signal from the RF tag in response to the excitation signal while the article is dry or prior to be used at initial time (t=0) and denoting as initial value RSSI(0) of the article; (d) wirelessly and timely detecting a received signal strength indicator (RSSI) of the response signal from the RF tag of the article, in response to the excitation signal and denoting as RSSI(t) of the article after being used for a usage time (t); and (e) determining the wetness (%) of the article at the usage time (t) by using the RSSI(0) and RSSI(t).

In the other words, the first wireless communication module 112 sends a detection signal through at least the first antenna module 113 so as to communicate with the RFID tag 50 disposed on the outer surface of the diaper 30. The RFID tag 50, after receiving the detection signal, will send a response signal. Accordingly, after sending the detection signal, the RFID reader 110 determines whether a response signal is received or information of the response signal is read so as to determine a wetness state of the diaper 30. In an embodiment, the processor unit 111 utilizes the first wireless communication module 112 (or the second wireless communication module 114) for determining whether a response signal indicating the diaper in a wetness state is received. For example, if the response signal is received, it is indicated that the diaper 30 is in a wetness state of getting wet; if the response signal is not received, it is indicated that the diaper 30 is not wet. In another embodiment, the RFID reader 110 reads the information of the response signal by the first wireless communication module 112 (or the second wireless communication module 114); the information of the response signal can be configured to include a wetness state value, for example, the value ranging from 0 to 100 to indicate the states from dry to fully wet, respectively; and the wetness state of the diaper 30 can then be obtained by reading the wetness state value in the response signal. In addition, in another embodiment, if the RFID reader 110, after sending a detection signal for one or more times, does not receive any response signal (or receiving the response signal which is less than a normal value or less than a lower limit of a normal range), it can further determine that the fall warning state of the user 20 with the diaper 30 is "abnormal" (which is another type of state of the care-receiver), which may indicate that the user 20 probably has left the position of the cushion (e.g., a mattress, a wheelchair cushion, or a seat cushion), or the user 20 has fallen or something wrong has happened to the user 20. In another embodiment, the system for detecting wetness of article used by a care-receiver further comprises an alarming unit (not shown) configured to notify a care-giver while wetness is higher than a preset value which is set by the care-giver. The alarming unit couples with the second wireless communication module 114; hence, the second antenna module 115 and the second wireless communication module 114 can be utilized for further sending a warning signal to call the caregiver through the alarm unit to observe what was happening on the spot, for the sake of safety.

Figure 4A:
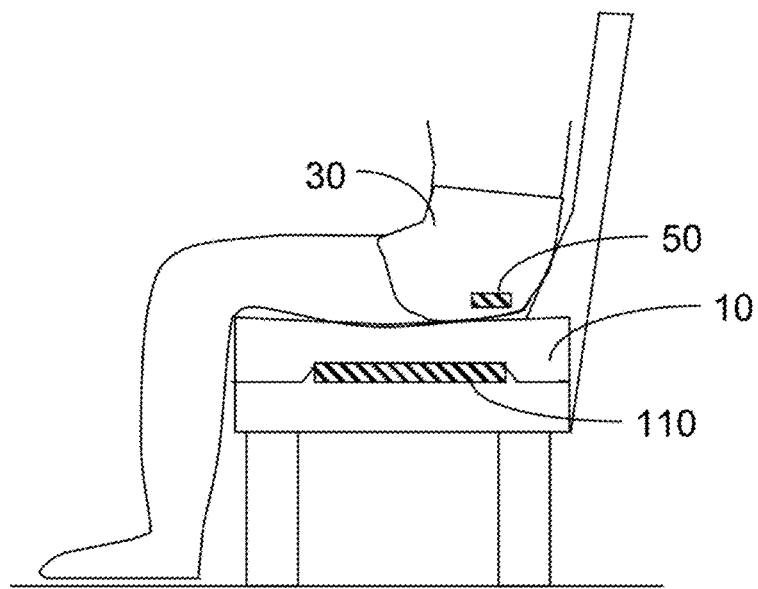
FIGS. 4A-4B illustrate schematic diagrams of an embodiment of the system for detecting wetness of article used by a care-receiver, disposed on different kinds of cushions.
Figure 4B:
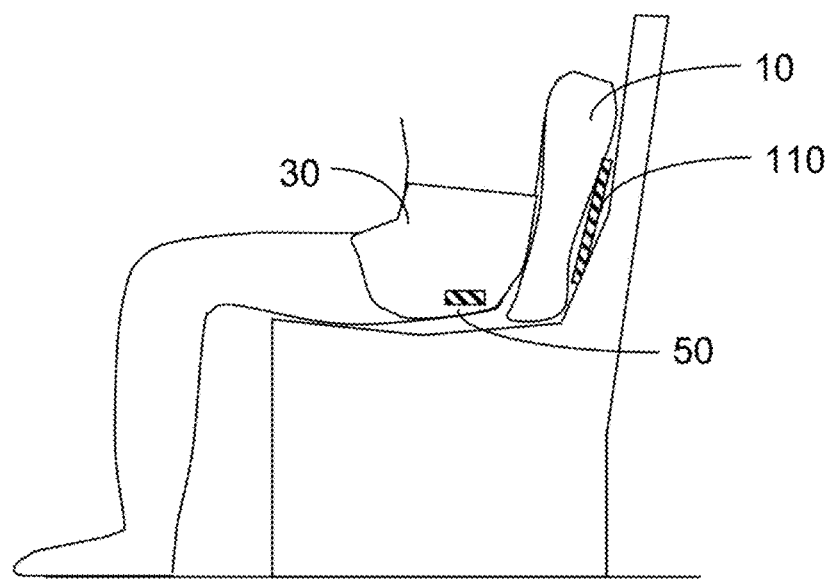

In addition to being disposed on the back of a mattress as exemplified above, the RFID reader 110 of the system for detecting wetness of article used by a care-receiver can be disposed on a back portion of any cushion (or the like), such as a wheelchair cushion, a back support cushion, a seat cushion, a lumbar cushion, and an air cushion. As shown in FIG. 4A, the RFID reader 110 is disposed under a cushion 10, such as a wheelchair cushion, a back support cushion, a seat cushion, and an air cushion, in some embodiments. As shown in FIG. 4B, the RFID reader 110 is disposed on a cushion 10, such as a lumbar cushion.

Figure 5:
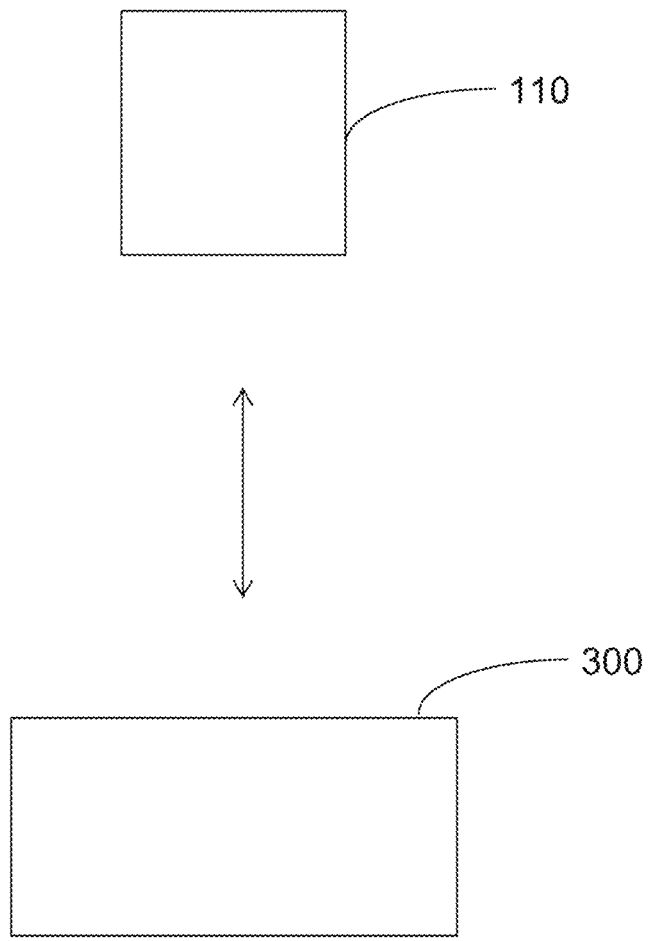
FIG. 5 is a schematic diagram illustrating the system for detecting wetness of article used by a care-receiver and a computing device of a healthcare center, according to an embodiment.

Referring to FIG. 1C, the second wireless communication module 114 of the RFID reader 110 is electrically coupled to the first wireless communication module 112 and the second antenna module 115. The first wireless communication module 112 communicates with a computing device in a wireless network by the second antenna module 115 and the second wireless communication module 114, and sends the state of the care-receiver to the computing device. The computing device refers to any electronic device with communication, computing power, such as cloud servers, LAN servers, desktop computers, laptop computers, tablet computers, and even smartphones, PDAs, pagers, dedicated communications equipment and so on. For example, FIG. 5 illustrates a RFID reader of the system for detecting wetness of article used by a care-receiver according to an embodiment communicating with a computer of a healthcare center. In an embodiment, an additional piece of wireless network equipment, such as a wireless router, can be utilized as a relay (or bridging) device between RFID reader 110 of the system for detecting wetness of article used by a care-receiver and the computing device 300. The second antenna module 115 and the second wireless communication module 114 can be implemented to be compliant with one or more wireless network standards, such as one or any combination of Zigbee, Wi-Fi, Bluetooth, mobile communication protocols (e.g., GSM, CDMA, WCDMA, UMTS, LTE and so on), satellite navigation system (e.g., GPS of the US, Galileo of EU, Beidou of People's Republic of China).

In addition to execute an application program to display the state of the care-receiver so as to remind the caregiver (nursing staff) for further processing, the computing device 300 can be further configured by an application program or program modules to record data, such as data about urination or defecation of the care-receiver (such as a bedridden person), which can be further tracked for indication of the care-receiver's condition and/or other application. In addition to the computing device 300, as exemplified above, a server or cloud data center can be utilized for the implementation of, for example, a software system communicating care-receivers and caregivers (e.g., HelloNurse™ system) so as to realize the functionality of recording data of caring or warning. Moreover, in yet another embodiment, the care-receiver's state can be provided to an electronic device, such as smart devices, of the care-receiver's caregiver or family member, being linked to the server or cloud data center through a network. In still another embodiment, the computing device 300 may be any smart devices, such as smartphones, tablet computers, smart watches, wearable devices, and the computing device 300 can be configured to execute an application program (APP) for use with the system for detecting wetness of article used by a care-receiver; and in this way, the caregiver or family member can obtain the care-receiver's state or record by using the computing device 300 through a wireless network (such as Wi-Fi) or Internet and so on. Hence, according to the embodiments of the invention, the system for detecting wetness of article used by a care-receiver can be applied to home care, in addition to healthcare centers, hospitals and so on.

Figure 6A:
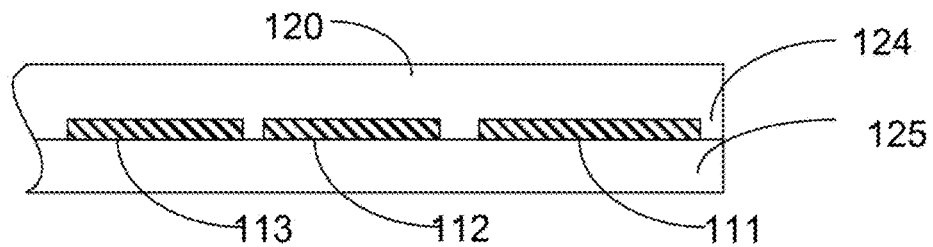
FIGS. 6A-6D illustrate cross-sectional views of embodiments of the system for detecting wetness of article used by a care-receiver.

Further, as illustrated in FIGS. 1A to 1C, the protective unit 120 covers the RFID reader 110, for accommodating the RFID reader 110 and for buffering external pressure on the RFID reader 110 so as to protect the RFID reader 110. FIG. 6A is a cross-sectional view illustrating an embodiment of the RFID reader 110 of the system for detecting wetness of article used by a care-receiver in FIG. 1B. As shown in FIG. 6A, the protective unit 120 includes a first protective layer 124 and a second protective layer 125. The RFID reader 110 (e.g., processor unit 111, the first antenna module 113, and the first wireless communication module 112) is disposed between the first protective layer 124 and the second protective layer 125. The first protective layer 124 and the second protective layer 125 are flexible and can be made from flexible materials such as any of foam, rubber, paper, plastarch material, or polymer materials, or combinations thereof. In an embodiment, the first protective layer 124 has a hardness greater than that of the second protective layer 125. However, any of the embodiments is for the sake of illustration only, without imposing any limitations on the implementation of the invention; the protective unit(s) may be formed by any material, the number of the protective layer, and/or the hardness of the protective layer may be implemented in various ways in view of the design and requirements for products.

In addition, the liftable parts (not shown) are provided on regions, in the first protective layer 124 or second protective layer 125 of the protective unit 120, corresponding to at least one portion of the RFID reader 110 (e.g., processor unit 111, the first antenna module 113, and the first wireless communication module 112). When any of the liftable part is lifted, processor unit 111, the first antenna module 113 or the first wireless communication module 112 of the RFID reader 110 can be exposed.

Figure 6B:
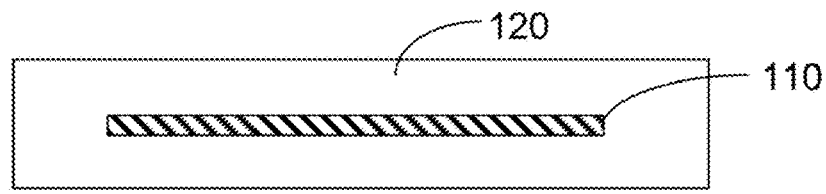
Figure 6C:
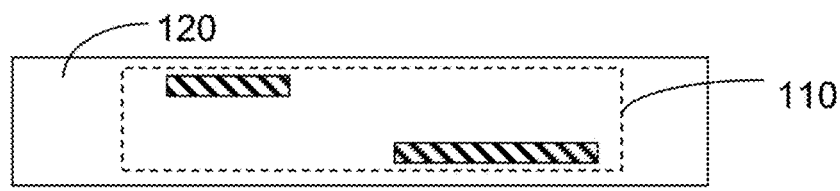
Figure 6D:
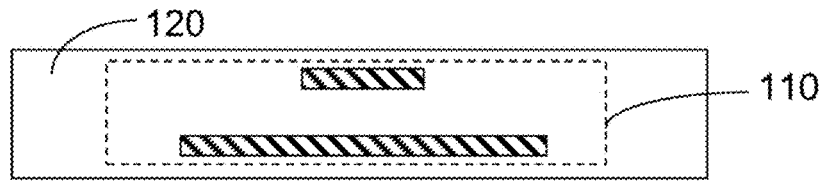

The arrangement of the protective unit and RFID reader may be changed in other ways. FIGS. 6B to 6D show cross-sectional views of other embodiments of the system for detecting wetness of article used by a care-receiver. As shown in FIG. 6B, the RFID reader 110 can be configured as a circuit board and embedded into the protective unit 120. As illustrated in FIG. 6C or 6D, the RFID reader 110 can be configured as two or more modules, and the modules can be embedded on different surfaces inside the protective unit 120.

Figure 7:
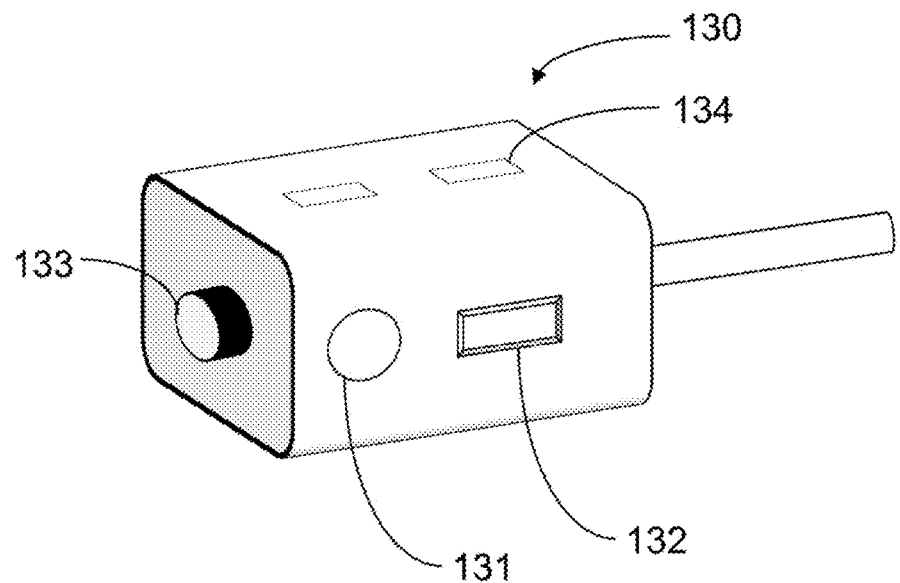
FIG. 7 illustrates a schematic diagram of an embodiment of an input part of the system for detecting wetness of article used by a care-receiver.

FIG. 7 illustrates a schematic diagram of an embodiment of an input part for the system for detecting wetness of article used by a care-receiver. As shown in FIG. 7, the input part 130 at least includes a power input 131, a communication interface 132 (e.g., an interface compliant to one of the data communication standards, such as RS-232, RS-422, or USB, USB2.0, USB3.0, and so on), and an input key 133 (e.g., a button key). In addition, the input part 130 may include an indicator 134 (e.g., an LED). For example, the power input 131 can be employed to an input terminal for AC or DC power for the system for detecting wetness of article used by a care-receiver; the communication interface 132 can be used for data transfer such as firmware update for the system for detecting wetness of article used by a care-receiver. In addition, the input key 133 can be used for power start-up, shutdown, and/or setting for the system for detecting wetness of article used by a care-receiver. One or more indicators 134 can be employed to indicate the operation state of the system for detecting wetness of article used by a care-receiver (e.g., normal, abnormal) or to indicate the state of the care-receiver (e.g., dryness, wetness, and so on). In addition, the above examples of the input part are optional and can be selectively implemented, without imposing any limitations on the implementation of the system for detecting wetness of article used by a care-receiver, and the system can be modified or configured in other ways. For example, in another embodiment, the RFID reader of the system for detecting wetness of article used by a care-receiver can be equipped with built-in batteries, and/or can be updated its firmware wirelessly by using the RFID reader of the system for detecting wetness of article used by a care-receiver, so that the input part may be unnecessary to be included therein.

Figure 8:
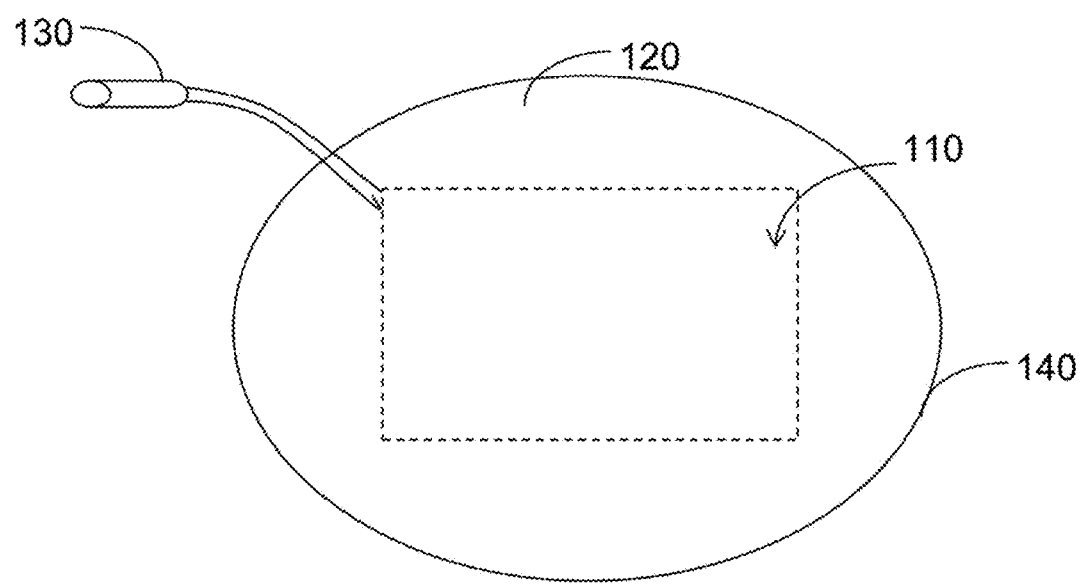
FIG. 8 illustrates a schematic diagram of an embodiment of the system for detecting wetness of article used by a care-receiver.

In addition, the protective unit and the protective cover of the system for detecting wetness of article used by a care-receiver according to the invention may be configured in any shapes. For example, in FIG. 8, the protective unit 120 and the protective cover 140 of the system for detecting wetness of article used by a care-receiver has its appearance configured to be round or oval shape.

The following further provides embodiments to illustrate how the system for detecting wetness of article used by a care-receiver determines a wetness state of the diaper 30 by way of communication with the RFID tag 50 attached to the diaper 30, as shown in FIG. 3A.

Referring to FIG. 3A, the RFID tag 50 includes an antenna 51 and a communication chip 52. The RFID reader issues an electromagnetic wave signal from the communication circuit under the cushion to be received by the antenna 51 and processed by the communication chip 52, and then receives a responsive signal back from the antenna 51.

Figure 3B:
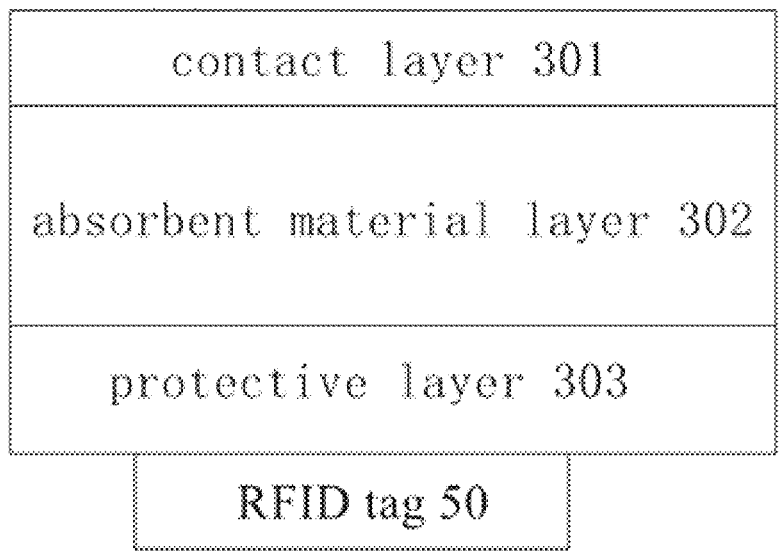
FIG. 3B illustrates an exemplified structure of the RFID tag of FIG. 3A.
Figure 3C:
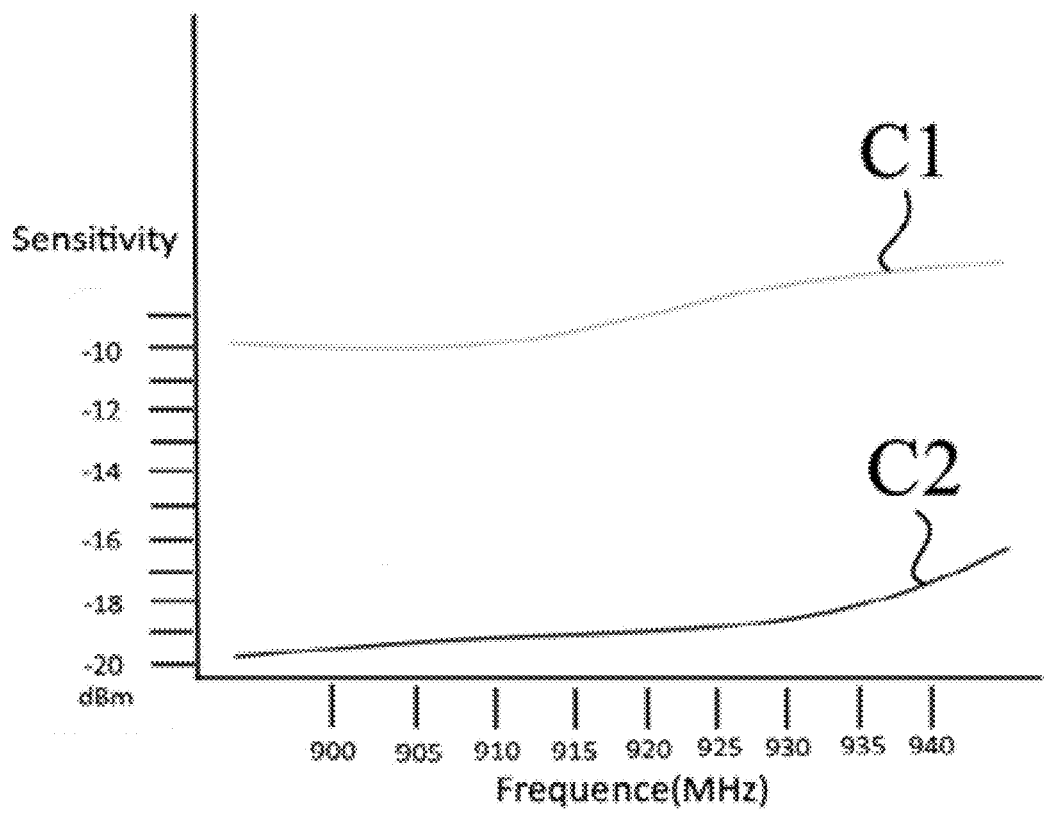
FIG. 3C is a sensitivity vs. frequency plot schematically illustrating the difference between the urine-filled absorbent material layer and the urine-free absorbent material layer.

In an embodiment, the RFID tag 50 as illustrated in FIG. 3A can be attached to an outer surface of an article which comprises at least an absorbent material, e.g. the diaper 30. Specifically, as shown in FIG. 3B, the article (or diaper 30) generally includes a contact layer 301, e.g. a fabric layer, an absorbent material layer 302, and a protective layer 303, e.g. an anti-leak layer; the contact layer 301 is in contact with the skin of the user, and the urine of the user may pass through the contact layer 301 and thus is absorbed by the absorbent material layer 302. The outer side of diaper 30 is a side not in contact with the skin of the user; such as an outer side of the anti-leak layer 303 of the diaper 30. It is understood by those skilled in the art that permittivity of a medium significantly varies with material of the medium. For example, the presence of a material with high permittivity in an electric field would significantly weaken the electric field. Therefore, when the absorbent material layer 302 of the diaper 30 is absorbing urine, the absorbent material layer 302 becomes a medium with changing transmittivity due to various impurities contained in urine. Since the tag 50 is attached to the anti-leak layer 303 adjacent to the absorbent material layer 302, the absorbent material layer 302 may serve as a substrate whose permittivity would affect the sensitivity of the antenna 51, and the wavelength of the electromagnetic wave signal varies accordingly. For example, as shown in the sensitivity vs. frequency plot of FIG. 3C, for the antenna 51, the urine-filled absorbent material layer 302 indicated by Curve C1 would cause reduced sensitivity compared with the urine-free absorbent material layer 302 indicated by Curve C2. Therefore, whether the diaper 30 is wet can be determined according to the detection result conducted by the state determination apparatus and the RFID tag 50. Since the RFID tag 50 is attached on the outer side of the diaper 30, the tag 50 can be removed from the discarded diaper and attached onto another clean diaper for reuse.

The detection with RFID reader 110 with the use of the RFID tag 50 will be described in more detail hereinafter.

The first wireless communication module 112 sends a detection signal through at least the first antenna module 113 so as to communicate with the RFID tag 50 on the diaper 30, and the a processor unit 111 configured to exhibit a signal strength indicator (RSSI) corresponding to a response signal from the RFID tag 50 in response to the sent detection signal (excitation signal), through the first antenna module 113, and denoting as RSSI(t) of the article after being used for a usage time (t), and the processor unit determines the wetness (%) of the article at the usage time (t) by calculating from following formula (I) by using the RSSI(0) and RSSI(t). In an embodiment, the RFID reader 110 stores a setting value, which is a numerical value of the wavelength of an electromagnetic wave (e.g., a response signal) to be transmitted by the RFID reader 110 when the inner side of the anti-leak layer is not wetted. In this embodiment, when the user of the diaper 30 urinates and the diaper 30 gets wet, the impedance value of the antenna of the RFID tag 50 will change. In this case, after receiving the detection signal, the RFID tag 50 sends a response signal which has a wavelength different from that of an electromagnetic wave signal sent by the RFID tag 50 when the inner side of the anti-leak layer has not got wet. Thus, the RFID reader 110, when receiving the response signal, can compare the response signal with the setting value so as to determine a wetness state of the diaper 30. In addition, in another embodiment, the setting value may set to a numerical value of the wavelength of an electromagnetic wave (e.g., a response signal) to be transmitted by the RFID reader 110 when the inner side of the anti-leak layer is wetted.

Figure 9:
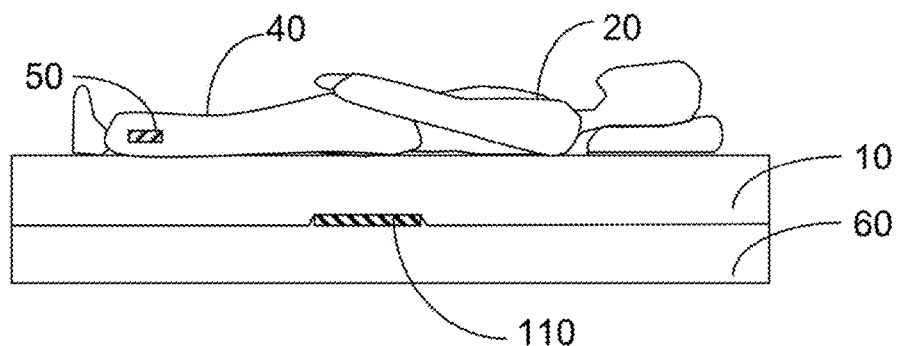
FIG. 9 is a schematic diagram illustrating an embodiment of using the system for detecting wetness of article used by a care-receiver with an RFID tag disposed on a pair of trousers.

In addition, the system for detecting wetness of article used by a care-receiver according to the invention can be utilized for determining a state of a care-receiver such as a fall warning state. In some embodiments, the RFID reader 110 can be disposed under the cushion and the RFID tag 50 can be disposed on the care-receiver; for example, the RFID tag 50 may be worn or attached to any clothes of the care-receiver (such as clothing, underwear, trousers, socks). For example, as shown in FIG. 9, an RFID tag 50 is attached to a leg of a pair of trousers 40 of the user 20 (i.e., the care-receiver). When the RFID reader 110 of the system for detecting wetness of article used by a care-receiver, after sending a detection signal for one or a plurality of times, does not receive any response signal (or receiving the response signal which is less than a normal value or less than a lower limit of a normal range), it can further determine that the fall warning state of the user 20 is "abnormal" (which is a type of state of the care-receiver), which may indicate that the user 20 probably has left the position of the cushion (e.g., a mattress, a wheelchair cushion, or a seat cushion), or the user 20 has fallen or something wrong has happened to the user 20. In another embodiment, the system detecting wetness of article used by further comprises an alarming unit (not shown) configured to notify a care-giver while wetness is higher than a preset value which is set by the care-giver. The alarming unit couples with the second wireless communication module 114; Hence, the second antenna module 115 and the second wireless communication module 114 can be utilized for further sending a warning signal to call caregivers to observe what was happening on the spot, for the sake of safety. Conversely, if the RFID reader 110 does receive a response signal (or receiving the response signal which is not less than a normal value or within a normal range), it can be determined that the fall warning state of the user 20 is "normal", indicating that the user 20 remains in the position (e.g., the position of the cushion).

The following provides some embodiments of how the RFID reader determines the state of the care-receiver. In implementation, the wetness-detecting result can be performed in the processor unit of the RFID reader.

In some embodiments, the RFID reader determines the state of the care-receiver as an abnormal state or a state of getting wet when the response signal is not received; the RFID reader determines the state of the care-receiver as a normal state or a state of getting dry when the response signal is received. In some examples, the first wireless communication module sends a detection signal through at least the first antenna module for at least one or a plurality of times so as to communicate with the RFID tag. In an example, the results of whether the response signal is received or not can be averaged in the case that the detection signal is sent for a plurality times so as to determine the state of the care-receiver. For example, a setting value (or a threshold value) can be taken as a reference that if the average occurrence of the response signal is lower than the setting value, it is determined that the state of the care-receiver is abnormal or is a state of getting wet; otherwise, it is determined that the state is normal or indicates that it is not wet.

In some embodiments, the processor unit of the RFID reader determines the state of the care-receiver as an abnormal state or a state of getting wet when the information including an identification code in the response signal is not received; the processor unit of the RFID reader determines the state of the care-receiver as a normal state or a state of getting dry when the information including the identification code in the response signal is received. For example, the identification code may be any code for identifying the RFID tag, such as electronic product code (EPC) or tag ID (TID) in a response signal. In some examples, the first wireless communication module sends a detection signal through at least the first antenna module for at least one or a plurality of times so as to communicate with the RFID tag. In an example, the results of whether the identification code in the response signal is received or not can be averaged in the case that the detection signal is sent for a plurality times so as to determine the state of the care-receiver. For example, a setting value (or a threshold value) can be taken as a reference that if the average occurrence of the identification code is lower than the setting value, it is determined that the state of the care-receiver is abnormal or is a state of getting wet; otherwise, it is determined that the state is normal or indicates that it is not wet.

Further, the identification code can be utilized as a tool for identification and/or calibration when the user changes the article (such as a new diaper or urine pad) or an RFID tag is changed so that the system identifies which RFID tag is to be detected. In a case, once a new diaper or RFID tag is used, the user can reset the RFID reader e.g., by pressing a button of the input part or instructing the RFID reader wirelessly, so that the RFID reader stores the identification code of the RFID tag for identification purpose, and/or stores an initial value (or state) for the RFID tag, which can be regarded as an initial value (or state) for the care-receiver and can be used in comparison with the values (or states) for the RFID detected afterwards for state determination.

In some embodiments, the RFID reader determines the state of the care-receiver based on signal strength of the response signal, such as a received signal strength indicator (RSSI) in the response signal. For example, the state of the care-receiver is a wetness state of an article on the care-receiver; and the RFID reader determines the wetness state as a state of getting wet when a value based on the RSSI is within a setting range (e.g., −30 dbm to −62 dbm). The value based the RSSI indicates a corresponding amount of moisture of the article (e.g., −30 dbm for being dry initially; and −62 dbm for fully wet). In some examples, the first wireless communication module sends a detection signal through at least the first antenna module for at least one or a plurality of times so as to communicate with the RFID tag. In an example, the results of the signal strength (e.g., RSSI) can be averaged in the case that the detection signal is sent for a plurality times (e.g., 2, 3, 4, 5, 8, 10, or 30, and so on) so as to determine the state of the care-receiver or the amount of moisture of the article on the care-receiver. The following table shows some calibration data for the relationship between the signal strength (e.g., values in dbm) and moisture; and according to the average value from data 1 and data 2, the relationship between RSSI and the water content of the article can be derived from the following formula (I):

$$\text{Water content (\%)} = \{RSSI(0) - RSSI(t)\}/0.32 \quad (I)$$

wherein the error value is ±5%;
RSSI(0) is a received signal strength indicator (RSSI) of the response signal from the RFID tag in response to the excitation signal while the article prior to be used at initial time (t=0); and
RSSI(t) is a received signal strength indicator (RSSI) of the response signal from the RFID tag in response to the excitation signal at a usage time (t) of the article being used.

Therefore, the processor unit determines the wetness (%) of the article at the usage time (t) by calculating from the formula (I) by using the RSSI(0) and RSSI(t).

The invention is not limited thereto; e.g. different number of scales (10, 20, 50, or 100 or more) can be obtained or made by way of experiment or calculation.

TABLE 1

| Moisture in the article (relative) | Data 1 RSSI (dbm) | Data 2 RSSI (dbm) | Average RSSI (dbm) |
|---|---|---|---|
| 0% (initial value) | −30 | −30 | −30 |
| 25% | −37 | −35 | −36 |
| 50% | −45 | −48 | 46.5 |
| 75% | −54 | −57 | 55.5 |
| 100% | −60 | −63 | 61.5 |

In other embodiments, the system for detecting wetness of article used by a care-receiver may be configured to have multiple antennas for communication with an RFID tag.

Figure 10:
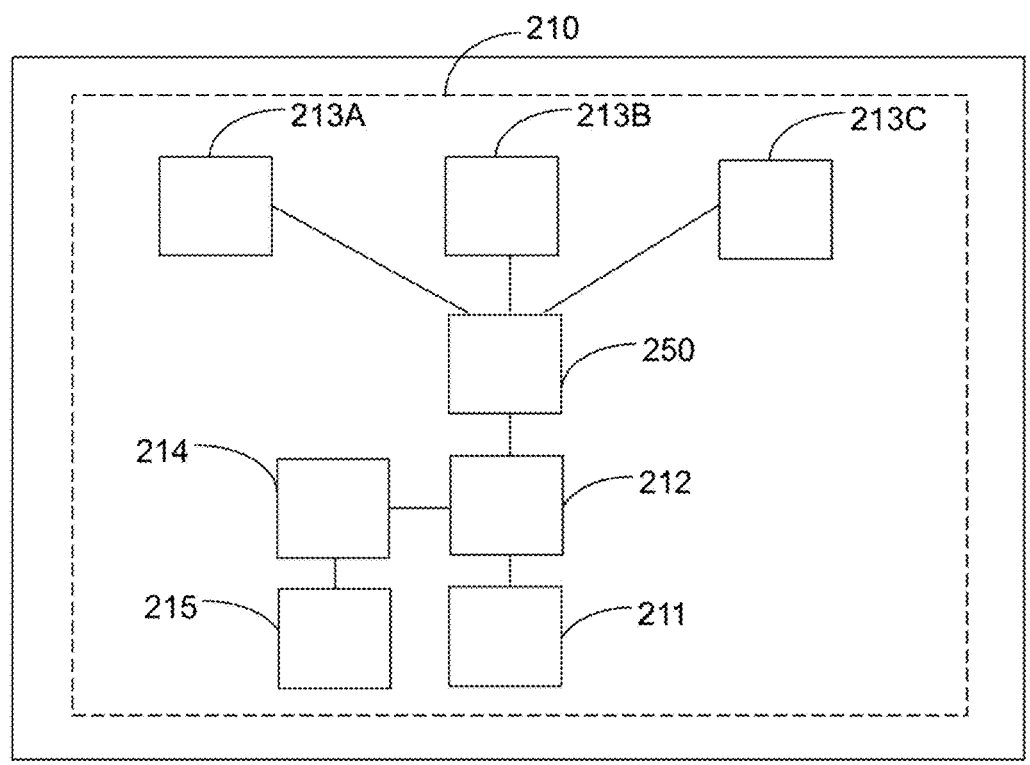
FIG. 10 illustrates a schematic diagram of another embodiment of a system for detecting wetness of article used by a care-receiver with multiple antennas for communication with an RFID tag.

FIG. 10 illustrates a schematic diagram of another embodiment of a RFID reader 210 of the system for detecting wetness of article used by a care-receiver with multiple antennas for communication with an RFID tag. The RFID reader 210 may be implemented based on any of the embodiments of the above system or any combination thereof. As compared to the embodiment of the system for detecting wetness of article used by a care-receiver in FIGS. 1A-1C, the main difference is that the RFID reader 210 in FIG. 10 includes multiple antennas for communication with an RFID tag. In FIG. 10, the RFID reader 210 having a plurality of first antenna modules (such as those indicated by 213A, 213B, and 213C), a first wireless communication module 212, a processor unit 211, a second antenna module 215, and a second wireless communication module 214. In addition, the RFID reader 210 includes a switch device 250, coupled between the first antenna modules (213A, 213B, and 213C) and the first wireless communication module 212. The first wireless communication module 212 can be configured to send a detection signal through the first antenna modules for a plurality of times (e.g., 2, 3, 4, 5, 8, 10, or 30, and so on) so as to communicate with an RFID tag used by the care-receiver (e.g., the RFID tag disposed on an article such as a diaper), wherein the detection signal sent to one of the first antenna modules may be in different frequency from the detection signal sent to another one. For instance, a detection signal is repeatedly sent for a number of times to each of the first antenna modules 213A, 213B, and 213C, respectively; the detection signal may indicate a request for an identification code and/or signal strength, or other parameter(s). After the detection signal is sent, the RFID reader (e.g., using the processor 211) can determine a state of the care-receiver based on the response signal accordingly, for example, in the way of any of the above embodiments (e.g., presence/absent of the response signal; using signal strength; or presence/absent of an identification code, and so on, by average or any statistic approach) or any combination thereof.

In some embodiment, the first antenna modules 213A, 213B, and 213C may be operated in different operating frequencies in a frequency band; they operate in three different frequencies in a frequency band of UHF from 902 MHz to 923.75 MHz or other frequency band, but the invention is not limited thereto. The first wireless communication module 212 can be configured to send a detection signal for a plurality of times through the first antenna modules 213A, 213B, and 213C in any order, for example, in a consecutive sequence, an alternating sequence, a random sequence, or any specific sequence, or any one of them repeatedly. In an example, the first wireless communication module 212 sends a detection signal for a plurality of times through the first antenna modules 213A, 213B, and 213C with the switch device 250 for switching the operating frequency and selecting the antenna modules in an order adopted.

Figure 11:
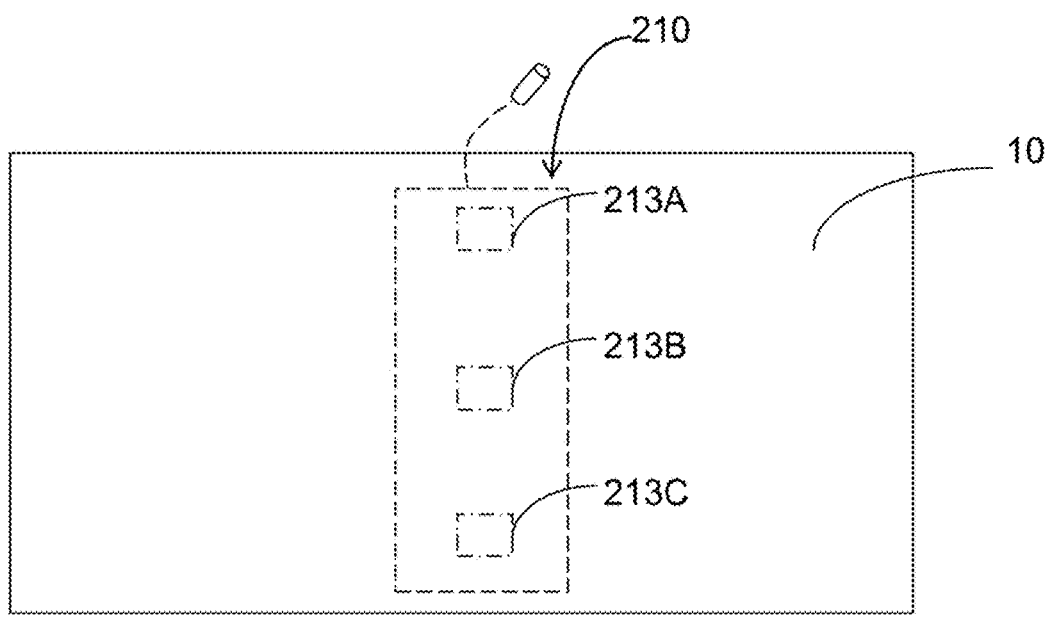
FIG. 11 illustrates a schematic diagram of an embodiment of the system for detecting wetness of article used by a care-receiver, disposed on a mattress.

FIG. 11 illustrates a schematic diagram of an embodiment of the FRID reader 210 of the system for detecting wetness of article used by a care-receiver, disposed on a mattress 10, wherein the blocks in dot-dashed lines indicate the first antenna modules 213A, 213B, and 213C. For example, the accuracy of the state determination can be further enhanced even if the user worn a diaper with an RFID tag as exemplified above moves oneself on the mattress 10 frequency during rest or sleeping. Further, it is noted that the embodiments in FIGS. 10 and 11 are for illustration; the invention is not limited thereto; e.g., the number and/or the positions and/or the types of the first antenna modules may be changed.

In addition, in another embodiment, the RFID reader of the system for detecting wetness of article used by a care-receiver, as exemplified in any of the above embodiments, can be disposed on a back of a cushion to perform state determination with respect to a care-receiver. In an embodiment, the RFID tag is disposed on an outer surface of an article, and the state of the care-receiver is, for example, a wetness state of the article of the care-receiver, as exemplified in any of the above embodiments such as that for FIG. 3. The article is a diaper or urine pad. In another embodiment, the RFID tag is worn on the care-receiver or attached to clothes of the care-receiver, and the state of the care-receiver is a fall warning state of the care-receiver; and this embodiment can be implemented by way of the above embodiments.

As disclosed above, the RFID reader of the system for detecting wetness of article used by a care-receiver according to the invention, is disposed on a back of a cushion (such as a mattress, seat cushion, back support cushion) to perform wetness detection with respect to a care-receiver, thus leading to higher accuracy of the wetness detection with respect to the care-receiver. In addition, as one embodiment above, the system for detecting wetness of article used by a care-receiver can be further utilized for determining whether the user leaves the position of the cushion (e.g., it may indicate that the user has left the bed or has fallen), thus providing additional functionality for caring. As such, the invention can greatly reduce the burden of work on the caregivers.

In addition, the FRID reader of the system for detecting wetness of article used by a care-receiver according to the invention, which is disposed under a cushion, does not require additional space for hardware arrangement on the room, thereby saving hardware space and cost. The efficiency of configuring the system for detecting wetness of article used by a care-receiver in hospitals, healthcare centers, or homes can be enhanced.

In addition, the users of diapers will not feel uncomfortable since the RFID reader of the system for detecting wetness of article used by a care-receiver is disposed on a back of a cushion (such as a mattress), not in contact with the body of the user. Since there is no noticeable special detection device equipped in the room, it will not bring additional sense of shame of being detected on the user. In addition, in one of the above embodiments, the system and method for detecting wetness of article used by a care-receiver informs the caregiver of the care-receiver's state by way of a wireless network linked to the computing device, so the matter making the user feeling shame, such as buzzing or flashing on the spot, will not happen.

In addition, the invention provides a system for detecting wetness of article used by a care-receiver, wherein the RFID tag is utilized for being disposed on an outer side of an article (diaper or urine pad), and the RFID reader of the system for detecting wetness of article used by a care-receiver is utilized for being disposed on a back of a cushion, so as to perform wetness detection of the user on a front side of the cushion. Therefore, there is no need to employ or design a complicated and expensive diaper and/or bed (or chair, wheelchair) with wetness detection. The efficiency of configuring the system for detecting wetness of article used by a care-receiver in hospitals, healthcare centers, or homes can be greatly enhanced.

It will be apparent to those skilled in the art that various modifications and variations can be made to the present disclosure without departing from the spirit and scope of the disclosure. Thus it is intended that the present disclosure cover the modifications and variations of this disclosure provided they come within the scope of the appended claims and their equivalents.

What is claimed is:

1. A system for detecting wetness of article used by a care-receiver, comprising: a radio frequency identity (RFID) reader, comprising: a first antenna circuit; a first wireless communication circuit, coupled to the first antenna circuit, configured to send a detection signal (excitation signal) through the first antenna circuit to a RFID tag, and configured to receive a response signal from the RFID tag in response to the sent detection signal, through the first antenna circuit, wherein the RFID tag is attached to an outer surface of an article used by the care-receiver, wherein the article comprises at least an absorbent material; and a processor unit configured to exhibit a signal strength indicator (RSSI) corresponding to a response signal from the RFID tag in response to the sent detection signal (excitation signal), through the first antenna circuit, and wherein the processor unit determines the wetness of the article at a usage time (t) by calculating a water content based on a difference between RSSI(0) and RSSI(t), wherein: RSSI(0) is a RSSI of the response signal from the RFID tag in response to the excitation signal at an initial time (t=0) prior to the article being used; and RSSI(t) is a RSSI of the response signal from the RFID tag in response to the excitation signal at the usage time (t) of the article being used.

2. The system for detecting wetness of article used by a care-receiver according to claim 1, which further comprises an alarm unit to notify a care-giver while when the wetness is higher than a preset value.

3. The system for detecting wetness of article used by a care-receiver according to claim 1, wherein the article comprises: an absorbent material layer having variable permittivity based on content of moisture in the absorbent material layer; a contact layer disposed at a side of the absorbent material layer for contact with skin of the care-receiver; and a protective layer disposed at an opposite side of the absorbent material layer to the contact layer.

4. The system for detecting wetness of article used by a care-receiver according to claim 3, wherein the article is a diaper or urine pad.

5. The system for detecting wetness of article used by a care-receiver according to claim 3, wherein the RFID tag is attached onto an outer surface of the protective layer opposite to the absorbent material layer.

6. The system for detecting wetness of article used by a care-receiver according to claim 1, which further comprises a protective unit that covers the RFID reader; wherein the protective unit includes a protection body and a liftable part on a region in the protective unit that corresponds to at least one portion of the RFID reader; wherein when the liftable part is lifted, the portion of the RFID reader is exposed.

7. The system for detecting wetness of article used by a care-receiver according to claim 6, wherein the protective unit further comprises:
 a first protective layer; and
 a second protective layer; wherein
  the RFID reader is disposed between the first protective layer and the second protective layer; the first protective layer and the second protective layer are flexible; the first protective layer has a hardness greater than that of the second protective layer.

8. The system for detecting wetness of article used by a care-receiver to claim 7, wherein the protective unit has a liftable part on a region, in the first protective layer or the second protective layer of the protective unit that corresponds to at least one portion of the RFID reader; wherein when the liftable part is lifted, the portion of the RFID reader is exposed.

9. The system for detecting wetness of article used by a care-receiver according to claim 1, which further comprising:
 an input part, coupled to the RFID reader, having at least one of a power input, a data interface, and an input key.

10. The system for detecting wetness of article used by a care-receiver according to claim 6, which further comprising:
 a protective cover, wherein the protective unit and the RFID reader are wrapped in the protective cover.

11. The system for detecting wetness of article used by a care-receiver according to claim 1, wherein the RFID reader further comprises:
 a second antenna circuit; and
 a second wireless communication circuit, electrically coupled to the first wireless communication circuit and the second antenna circuit; wherein
  the first wireless communication circuit utilizes the second antenna circuit and the second wireless communication circuit so as to communicate with a computing device in a wireless network, and sends a state of the care-receiver to the computing device.

12. The system for detecting wetness of article used by a care-receiver according to claim 1, wherein the RFID reader further comprises
 a plurality of the antenna circuits that comprise the first antenna circuit; and
 a switch device, coupled between the plurality of antenna circuits and the first wireless communication circuit.

13. The system for detecting wetness of article used by a care-receiver according to claim 12, wherein the first wireless communication circuit sends a detection signal through at least the first antenna circuit for one or more times to communicate with the RFID tag.

14. The system for detecting wetness of article used by a care-receive according to claim 1, wherein the RFID reader is configured to be disposed on a back of a cushion.

15. The system for detecting wetness of article used by a care-receiver according to claim 14, wherein the cushion is one of a mattress, a wheelchair cushion, a back support cushion, a seat cushion, a lumbar cushion, and an air cushion.

16. A method for detecting wetness of article used by a care-receiver, comprising the steps of:
 attaching a radio frequency identity (RFID) tag onto outer surface of an article to be detected, wherein the article includes an absorbent material, and the RFID tag is configured to exhibit different sensitivities to an electromagnetic wave signal in response to different permittivities of the article;
 exciting a RFID tag with an excitation signal (ES);
 wirelessly detecting a first received signal strength indicator (RSSI) of the response signal from the RFID tag in response to the excitation signal while the article is dry or prior to be used at an initial time (t=0); and
 wirelessly detecting a second RSSI of the response signal from the RFID tag in response to the excitation signal after the article is used for a usage time (t); and
 determining the wetness of the article at the usage time (t) by calculating a water content based on a difference between the first RSSI and the second RSSI.

17. The method for detecting wetness of article used by a care-receiver according to claim 16, wherein the article comprises:
 an absorbent material layer having variable permittivity based on the content of moisture in the absorbent material layer;
 a contact layer disposed at a side of the absorbent material layer for contact with skin of the care-receiver; and
 a protective layer disposed at an opposite side of the absorbent material layer to the contact layer.

18. The method for detecting wetness of article used by a care-receiver according to claim 17, wherein the absorbent material layer and the RFID tag are not in contact with each other.

19. The system for detecting wetness of article used by a care-receiver according to claim 1, wherein the processor unit determines the wetness of the article at the usage time (t) as a water content percentage by dividing the difference between the RSSI(0) and the RSSI(t) by 0.32.

20. The method according to claim 16, wherein calculating the wetness of the article at the usage time (t) comprises determining a water content percentage by dividing the difference between the first RSSI and the second RSSI by 0.32.

* * * * *